United States Patent [19]

Hsu

[11] Patent Number: 5,385,902
[45] Date of Patent: Jan. 31, 1995

[54] IODOPROPARGYLATED OXALIC DERIVATIVES AS ANTIMICROBIAL AGENTS

[75] Inventor: Adam C. Hsu, Lansdale, Pa.

[73] Assignee: Rohm and Haas Company, Philadelphia, Pa.

[21] Appl. No.: 116,171

[22] Filed: Sep. 1, 1993

[51] Int. Cl.⁶ .................... A01N 37/14; A01N 43/84; C07C 69/36; C07D 295/185
[52] U.S. Cl. .................... 514/237.5; 514/212; 514/227.5; 514/275; 514/315; 514/423; 514/430; 514/538; 514/547; 514/548; 540/607; 544/58.4; 544/171; 544/332; 546/245; 548/200; 548/540; 549/72; 560/41; 560/43; 560/51; 560/146; 560/193; 560/197
[58] Field of Search ................ 544/171; 560/51, 197; 514/237.5

[56] References Cited

FOREIGN PATENT DOCUMENTS 7914871 11/1979 Japan .

Primary Examiner—Robert W. Ramsuer
Attorney, Agent, or Firm—Michael B. Fein

[57] ABSTRACT

Antimicrobial compounds of the formula

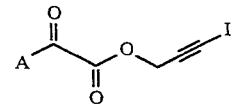

wherein A is selected from the group consisting of alkyl; phenyl; alkoxy; phenoxy; benzyloxy; monoalkylamino; dialkylamino; cyclic amino, anilino; heterocyclic; amino substituted with heterocyclic ring, methods of making and using said compounds, and compositions comprising said compounds are disclosed.

9 Claims, No Drawings

IODOPROPARGYLATED OXALIC DERIVATIVES AS ANTIMICROBIAL AGENTS

I. BACKGROUND OF THE INVENTION

A. Field of the Invention

This invention relates to novel antimicrobial compounds and their use.

B. Description of the Prior Art

Jpn Kokai 79,148,718, 1979 (CA(92): 214902u) discloses compounds having the following general structure.

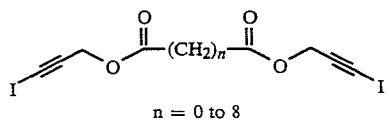

n = 0 to 8

II. SUMMARY OF THE INVENTION

Many of the antimicrobials of the prior art are ineffective against Gram negative bacteria, have toxicity, and/or environmental problems. It is an object of this invention to provide antimicrobial compounds which have excellent activity against a broad spectrum of fungi and bacteria, and have favorable toxicological and environmental profiles.

These objects and others are achieved by the present invention which comprises compounds having Antimicrobial activity having the formula:

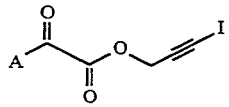

wherein A is selected from the group consisting of substituted or unsubstituted($C_1$-$C_{20}$)alkyl; substituted or unsubstituted phenyl; substituted or unsubstituted (C7-C10)aralkyl; substituted or unsubstituted ($C_1$-$C_{20}$) alkoxy; substituted or unsubstituted phenoxy; substituted or unsubstituted benzyloxy; mono($C_1$-$C_{10}$)alkylamino; di($C_1$-$C_{10}$)-alkylamino; ($C_5$-$C_7$)cyclic amino; substituted or unsubstituted anilino; (C5-C7)heterocyclo; and amino substituted with heterocyclic ring.

III. DETAILED DESCRIPTION OF THE INVENTION AND THE PREFERRED EMBODIMENTS

By substituted alkyl is meant an alkyl group having one or more of its hydrogens replaced with another substituent group. Examples of suitable substituent groups are nitro, halo, cyarto, hydroxy, ($C_1$-$C_3$)alkoxy, amino, mono($C_1$-$C_3$)alkylamino, di($C_1$-$C_3$)alkylamino, ($C_1$-$C_3$)alkylthio, and mercapto. Examples of suitable alkyl groups include methyl, ethyl, propyl, butyl, octyl, methoxymethyl, and methoxyethyl.

By substituted phenyl is meant a phenyl group having one or more of its hydrogens replaced with another substituent group. Examples of suitable substituent groups include ($C_1$-$C_3$)alkyl, ($C_1$-$C_3$)alkoxy, hydroxy, nitro, halo, cyano, ($C_1$-$C_3$)alkylthio, and mercapto. Examples of substituted phenyl groups which characterize the compounds of the invention include 4-methylphenyl, 2-chlorophenyl, 3-chlorophenyl, 4-chlorophenyl, 2-methoxyphenyl, and 4-methoxyphenyl.

By substituted phenoxy is meant a phenoxy group having one or more of its hydrogens replaced with another substituent group. Examples of suitable substituent groups include ($C_1$-$C_3$)alkyl, ($C_1$-$C_3$)alkoxy, nitro, halo, cyano, ($C_1$-$C_3$)alkylthio.

By substituted benzyloxy is meant a benzyloxy group having one or more of its hydrogens on the phenyl ring replaced with another substituent group. Examples of suitable substituent groups include ($C_1$-$C_3$)alkyl, ($C_1$-$C_3$)alkoxy, nitro, halo, cyano, ($C_1$-$C_3$)alkylthio.

By substituted aralkyl is meant an aralkyl group having one or more of its hydrogens replaced with another substituent group. Examples of suitable substituent groups include ($C_1$-$C_3$)alkyl, ($C_1$-$C_3$)alkoxy, hydroxy, nitro, halo, cyano, ($C_1$-$C_3$)alkylthio, and mercapto. Examples of substituted aralkyl groups which characterize the compounds of the invention include benzyl, 4-methylbenzyl, and phenethyl.

By substituted alkoxy is meant an alkoxy group having one or more of its hydrogens replaced with another substituent group. Examples of suitable substituent groups are nitro, halo, cyano, hydroxy, ($C_1$-$C_3$)alkyl,($C_1$-$C_3$)alkoxy, amino, mono($C_1$-$C_3$)alkylamino, di($C_1$-$C_3$)alkylamino, ($C_1$-$C_3$)alkylthio, and mercapto. Examples of suitable alkoxy groups include methoxy, ethoxy, propoxy, butoxy, methoxymethoxy, and methoxyethoxy.

By mono- and di-substituted amino is meant an amino group having one or more of its hydrogens replaced with another substituent group. Examples of suitable substituent groups include ($C_1$-$C_{10}$)alkyl, (C7-$C_{10}$)aralkyl, phenyl, and substituted phenyl. Examples of substituted amino groups which characterize the compounds of the invention include methylamino, dimethylamino, ethylamino, diethylamino, propylamino, isopropylamino, octylamino, benzylamino, anilino, 3-methylanilino, 4-methylanilino, 2-chloroanilino, 3-chloro-anilino, 4-chloroanilino, 2-fluoro-4-chloro-5-propargyloxyanilino, and 4,6-dimethylpyrimidinylamino.

By cyclic ammo is meant groups such as morpholino, methylmorpholino, dimethyhnorpholino, tetramethylene-imino, piperidino, methylpiperidino, dimethylpiperidino, thiazolidino, and methylthiazolidino.

By amino substituted with a heterocyclic ring is meant an amino group with one or both of its hydrogens replaced with a ($C_5$-$C_7$)cyclic ring containing at least one heteroatom. Examples of suitable heterocycles include thienyl, morpohlino, methylmorpholino, dimethylmorpholino, tetramethyleneimino, piperidino, pyrrolidino, methylpiperidino, dimethylpiperidino, thiazolidino, methylthiazolidino, tetramethylmorpholino, furano, and thiazino.

Preferred compounds (and compound numbers) of the invention are:

1. Benzoyl formic acid 3-iodo-prop-2-ynyl ester.
2. n-Octyl oxalamic acid 3-iodo-prop-2-ynyl ester.
3. n-Propyl oxalamic acid 3-iodo-prop-2-ynyl ester.
4. Thienyl-2-carbonyl formic acid 3-iodo-prop-2-ynyl ester.
5. Ethyl 3-iodo-prop-2-ynyl oxalate.
6. Methyl 3-iodo-prop-2-ynyl oxalate.
7. Phenyl oxalamic acid 3-iodo-prop-2-ynyl ester.
8. Pyrrolidine-1-yl-oxo acetic acid 3-iodo-prop-2-ynyl ester.
9. 3-Methyl-phenyl oxalamic acid 3-iodo-prop-2-ynyl ester.

10. 2-Fluoro-4-chloro-5-propargyloxyphenyl oxalamic acid 3-iodo-prop-2-ynyl ester.
11. 4,6-dimethyl-pyrimidin-2-yl oxalamic acid 3-iodo-prop-2-ynyl ester.
12. Piperidine-1-yl-oxo acetic acid 3-iodo-prop-2-ynyl ester.
13. Morpholin-4-yl-oxo-acetic acid 3-iodo-prop-2-ynyl ester.
14. Hexamethylene-imino-1-yl-oxo-acetic acid 3-iodo-prop-2-ynyl ester.
15. 2,6-Dimethyl-morpholin-4-yl-oxo-acetic acid 3-iodo-prop-2-ynyl ester.
16. 4-Methyl-phenyl oxalamic acid 3-iodo-prop-2-ynyl ester.
17. 4-Chloro-phenyl oxalamic acid 3-iodo-prop-2-ynyl ester.
18. 2-Chloro-phenyl oxalamic acid 3-iodo-prop-2-ynyl ester.
19. 3-Chloro-phenyl oxalamic acid 3-iodo-prop-2-ynyl ester.
20. [1,4]-Thiazinan-4-yl-oxo-acetic acid 3-iodo-prop-2-ynyl ester.
21. Thiazolidine-3-yl-oxo-acetic acid 3-iodo-prop-2-ynyl ester.
22. Phenyl 3-iodo-prop-2-ynyl oxalate.
23. Benzyl 3-iodo-prop-2-ynyl oxalate.
24. Benzyl oxalamic acid 3-iodo-prop-2-ynyl ester.

Table 1 shows the melting points and A substituents for the listed compounds.

TABLE 1

Melting Points and Structures

| Compound No. | A | Melting Point (°C.) |
|---|---|---|
| 1 | 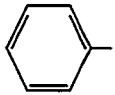 | 48–50 |
| 2 | C$_8$H$_{17}$—NH— | 89–92 |
| 3 | C$_3$H$_7$—NH— | 89–92 |
| 4 | 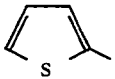 | 109–111 |
| 5 | EtO— | 63–65 |
| 6 | MeO— | 75–77 |
| 7 | 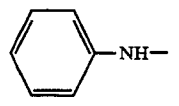 | 144–147 |
| 8 | 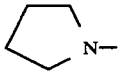 | 102–107 |
| 9 | 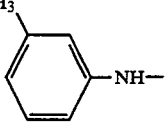 | 170–172 |
| 10 | 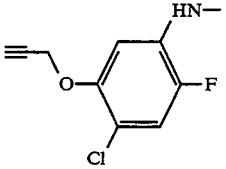 | 151–153 |
| 11 | 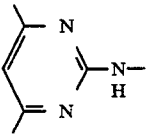 | 145–150 |
| 12 | 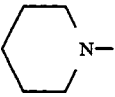 | 80–85 |
| 13 | 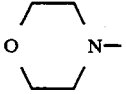 | 106–109 |
| 14 | 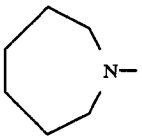 | 50–55 |
| 15 | 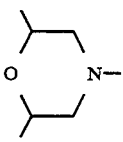 | 95–98 |
| 16 | 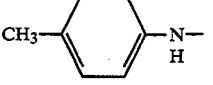 | 169–170 |
| 17 | 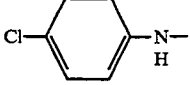 | 157–159 |
| 18 | 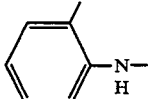 | 140–144 |
| 19 | 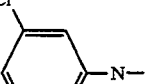 | 178–180 |
| 20 | 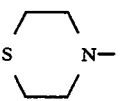 | 71–74 |

TABLE 1-continued

Melting Points and Structures

| Compound No. | A | Melting Point (°C.) |
|---|---|---|
| 21 | [thiazolidine ring with S and N–] | 82–85 |
| 22 | [phenyl-O–] | 79–93 |
| 23 | [benzyl-O–] | 45–49 |
| 24 | [benzyl-NH–] | 93–98 |

Compounds of the invention can be prepared by the following reaction:

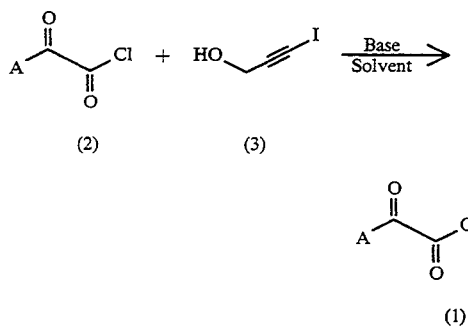

(2)   (3)   →   (1)

One equivalent of iodopropargyl alcohol (3), which is known and can be prepared by following the method in the literature, is reacted with a variety of oxalyl chlorides of the formula (2) in a solvent in the presence of a base at the temperature between 0° to 25° C.

Some of the compounds of formula (2) are commercially available. For example, when A=EtO, compound (2) is ethyl oxalyl chloride. Alternatively, compounds of the formula (2) can be prepared from oxalyl chloride of the formula (4) by reaction with A-H of the formula (6) according to the following reaction:

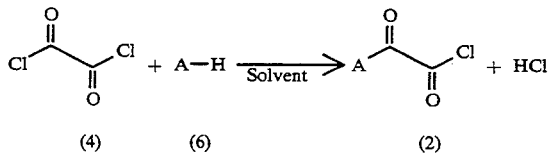

(4)   (6)   (2)

Compounds of the formula (2) are subsequently reacted with iodopropargyl alcohol in the presence of base in a suitable solvent to produce the compounds of this invention, formula (1). Oxalyl chloride (formula (4)) is commercially available. Compounds of the formula (6) are generally commercially available.

Compounds of the formula (1) of this invention can also be prepared from the following reaction:

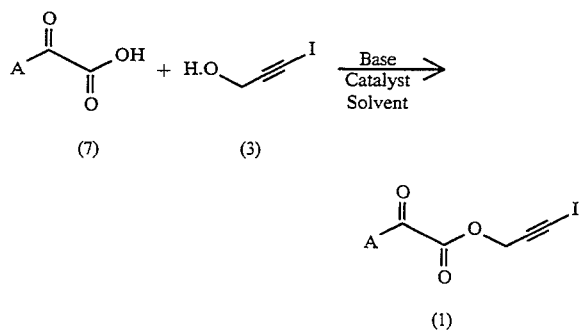

(7)   (3)   →   (1)

Iodopropargyl alcohol is reacted with compounds of the formula (7) in the presence of a base and a catalyst in a suitable solvent at the temperature of 0° to 25° C. Compounds of the formula (7) are commercially available (for example, when A=phenyl, compound (7) is benzoyl formic acid) or can be prepared by known methods in the literature.

The compounds of the invention can be used to inhibit the growth of microbes by introducing a microbicidally effective amount of one or more of said compounds onto, into, or at a locus subject to microbial attack. Loci such as wood, paint, adhesive, glue, paper, pulp/paper slurries, textile, leather, plastics, cardboard, lubricants, cosmetics, food, caulking, feed, and industrial cooling water can be protected.

The amount of compound suitable is about 5 to about 300 ppm based on weight of said locus. Generally, the microbicide is applied in a carrier such as water, solvent, or the like.

In addition to utility in the protection of industrial materials, some of the compounds of the invention have utility as plant fungicides or bactericides. Microorganisms which are to be controlled include Gram positive and Gram negative bacteria, fungi, yeasts, algae, viruses, and the like.

The following examples illustrate a few embodiments of the invention.

EXAMPLES

EXAMPLE 1

Synthesis of Benzoyl formic acid 3-iodo-prop-2-ynyl ester (Compound #1)

To a cold, stirred solution of benzoyl formic acid (1.5 g, 0.01 mole) in methylene chloride (75 mL) at 4° C. were added iodopropargyl alcohol (1.9 g, 0.0105 mole) followed by 4-dimethylaminopyridine (0.122 g, 0.001 mole) and ethyl-(3-dimethylaminopropyl)carbodiimide hydrochloride (2 g, 0.0104 mole). After stirring at 0° to 10° C. for one hour, the reaction mixture was diluted with methylene chloride (100 mL) and was washed with water (3×50 mL) and brine. The organic layer was dried over sodium sulfate, filtered, and concentrated to a residue. The residue was triturated with hexane and the product, a pale yellow solid, was collected by suction-filtration yielding 1.75 g (60%), mp=48°–50° C. An nmr spectrum showed the desired compound.

EXAMPLE 2

Synthesis of Ethyl 3-iodo-prop-2-ynyl oxalate (Compound #5)

To an ice cold, stirred solution of iodopropargyl alcohol (2 g, 0.012 mole) in methylene chloride (50 mL) was added triethylamine (1.23 g, 0.012 mole). To the above solution was added dropwise over a 10 min period a solution of ethyl oxalyl chloride (1.65 g, 0.012 mole) in methylene chloride (20 mL). When the addition is complete, the mixture was allowed to stir at 0° to 5° C. for 10 min, then at room temperature for one hour. Thin layer chromatography (TLC) (EtOAc:Hexane=1:3) showed the reaction was completed. The reaction mixture was diluted with 50 mL of methylene chloride and washed with water (2×50 mL) and brine. The organic layer was dried over MgSO$_4$, filtratered, and evaporated to give a residue. The residue was slurried with hexane and the solid was collected by suction-filtration affording 2.2 g (64.7%) as a white solid. mp=63°–65° C. An nmr spectrum showed the desired compound.

EXAMPLE 3

Synthesis of 4,6-Dimethyl-pyrimidin-2-yl oxalamic acid 3-iodo-prop-2-ynyl ester (Compound #11)

To an ice-cold, stirred solution of oxalyl chloride (1.27 g, 0.01 mole) in THF (30 mL) under nitrogen was added, in one portion, a solution of iodopropargyl alcohol (1.81 g, 0.01 mole) in THF (10 mL). After stirring for 30 min at 0° to 5 ° C., a solution of 2-amino-4,6-dimethyl-pyrimidine (1.11 g, 0.009 mole) and triethylamine (2 g, 0.02 mole) in THF (30 mL) was added dropwise over a 10 min period. After the addition was complete, the reaction mixture (a white suspension) was stirred at room temperature for 40 min. The reaction mixture was then poured into ice cold water (250 mL) and the precipitate was collected by suction-filtration, washed with water, and dried in air. A recrystallization of the above crude product with methylene chloride/hexane yielded 2.1 g (58.7%) of pure product, mp=145°–150° C. An nmr spectrum (DMSO-d$_6$) showed the desired compound.

EXAMPLE 4

Synthesis of 3-Methyl-phenyl oxalamic acid 3-iodo-prop-2-ynyl ester (Compound #9)

To an ice-cold, stirred solution of oxalyl chloride (2.54 g, 0.02 mole) in THF (30 mL) under nitrogen was added a solution of iodopropargyl alcohol (3.62 g, 0.02 mole) in THF (10 mL). After stirring for 50 min at 0° to 5° C., a solution of m-toluidine (1.93 g, 0.018 mole) and triethylamine (4 g, 0.04 mole) in THF (30 mL) was added dropwise over a 20 min period. Following the addition, the reaction mixture (a white suspension) was stirred at room temperature for 2 hr. and then poured into ice cold water (500 mL). The precipitate was collected by suction-filtration, washed with water, and was dried in air to give 6.5 g of a pale green solid. A recrystallization of the above crude product with methylene chloride/hexane yielded 3.7 g (54%) of 3-methylphenyl oxalamic acid 3-iodo-prop-2-ynyl ester as a pure product, mp=170°–172° C. An nmr spectrum (DMSO-d$_6$) showed the desired compound.

EXAMPLE 5

Biological Activity

Biocidal (bactericidal and fungicidal) evaluations were carried out.

A minimum inhibitory concentration (MIC) value is obtained using a broth, two-fold serial dilution test performed as follows: A stock solution or dispersion of the test compound, typically at a concentration of 1%, is made in a 5:3:2 solvent solution of acetone, methanol, and water. A volume of the stock solution is dispensed into culture media to give an initial starting test concentration of 500 ppm compound.

When the test is ready to be done, each vessel in the dilution series, except the first vessel, contains an equal volume of compound free broth. The first vessel contains twice the volume of broth with the starting concentration of test compound. One half of the broth from the first vessel is transferred to the second vessel. After being mixed, one half the resulting volume is removed from the second vessel and transferred to the third vessel. The entire cycle is repeated sufficiently to give a series of concentrations amounting to 500, 250, 125, 63, 31, 16, 8, and 4, 2, 1, 0.5, 0.25 ppm respectively.

Each vessel is then inoculated with a cell suspension of the appropriate test organism. Bacteria are grown in broth, fungi on agar slants for a time and at a temperature appropriate to the species being tested, and algae are a mixture of green algae and blue-green bacteria grown in a nutrient media. At the end of the growth period, in the case of bacteria, the broth is vortexed to disperse the cells.

In the case of fungi, the spores are harvested by pipetting water onto the slant and dislodging the spores with a sterile loop. The cell/spore suspension is standardized by controlling incubation time, temperature, and the volume of the diluent. The suspension is then used to inoculate the vessels containing the broth compound.

The vessels are then incubated at the appropriate temperature. After the incubation, the vessels are examined for growth/no growth. The minimum inhibitory concentration (MIC) is defined as the lowest concentration of compound that results in complete inhibition of growth of the test organism.

The organisms tested to demonstrate biocidal activity are shown in the Table 2:

TABLE 2

| Microorganisms Used in the Biocides Tests | | | |
|---|---|---|---|
| Name | GRAM | ATCC | Abbreviation used |
| BACTERIA | | | |
| 1. Pseudomonas aeruginosa | (−) | 15442 | Psae |
| 2. Staphylococcus aureus | (+) | 6538 | Saur |
| 3. Escherichia coli | (−) | 11229 | Ecol |
| FUNGUS | | | |
| 4. Aspergillus niger | | 6275 | Anig |

The results of minimum inhibitory concentration (MIC) tests of compounds of this invention are shown in Table 3.

TABLE 3

| Compound | Biocidal MIC Results | | | | | | |
|---|---|---|---|---|---|---|---|
| | Psae | | Ecol | | Saur | | Anig |
| No. | M9G | TSB | M9G | TSB | M9G | TSB | TSB |
| 1 | 8 | 125 | 63 | 63 | 125 | 125 | <0.25 |

TABLE 3-continued

| Compound No. | Biocidal MIC Results | | | | | | |
|---|---|---|---|---|---|---|---|
| | Psae | | Ecol | | Saur | | Anig |
| | M9G | TSB | M9G | TSB | M9G | TSB | TSB |
| 2 | >500 | >500 | >500 | >500 | 32 | 63 | 1 |
| 3 | 63 | 125 | 125 | 63 | 63 | 125 | 1 |
| 4 | 250 | 250 | 250 | 500 | 125 | 125 | 2 |
| 5 | 32 | 63 | 63 | 63 | 32 | 63 | 0.5 |
| 6 | 63 | 125 | 63 | 125 | 125 | 125 | 1 |
| 7 | 125 | 63 | 250 | 125 | 125 | 250 | 2 |
| 8 | 63 | 63 | 16 | 8 | 16 | 32 | 2 |
| 9 | 500 | 500 | >500 | >500 | 500 | 500 | 2 |
| 10 | 500 | >500 | 250 | >500 | 500 | 500 | 8 |
| 11 | 32 | 125 | 63 | 16 | 250 | 250 | 4 |
| 12 | 125 | 250 | 4 | 32 | 4 | 8 | <0.25 |
| 13 | 125 | 250 | 63 | 63 | 63 | 63 | 1 |
| 14 | 125 | 500 | 4 | 32 | 4 | 4 | <0.25 |
| 15 | 63 | 125 | 4 | 32 | 32 | 63 | <0.25 |
| 16 | >500 | 250 | >500 | 250 | >500 | 250 | 0.5 |
| 17 | >500 | >500 | >500 | >500 | >500 | >500 | 1 |
| 18 | >500 | >500 | >500 | >500 | >500 | >500 | 1 |
| 19 | >500 | >500 | >500 | >500 | >500 | >500 | 1 |
| 20 | 500 | 250 | 64 | 64 | 250 | 250 | 2 |
| 21 | 125 | 250 | 125 | 125 | 250 | 250 | 8 |
| 22 | 125 | 125 | 250 | 125 | 250 | 250 | 8 |
| 23 | 125 | 125 | 125 | 125 | 250 | 250 | 2 |
| 24 | 125 | 125 | 64 | 64 | 250 | 250 | 2 |

EXAMPLE 6

Agricultural Fungicidal Activity

Compounds of the invention were tested in a fungicide in vitro screen. This screen is designed to provide information regarding the activity and spectrum of pathogen sensitivity on compounds. The compounds were tested against the following 8 organisms.

RHI *Rhizoctonia solani*
PYT *Pythium ultimum*
COL *Colletotrichum lagenarium*
HEL *Helminthosporium sativum*
PHY *Phytophthora capsici*
BOT *Botrytis cinerea*
PYR *Pyricularia oryzae*
SEP *Septoria nodorum*

The test employs an automated (Zymark Robot) microtiter bioassay system. Growth is measured spectrophotometrically with a Biotek microtiter plate reader, and corrected for absorbance due to the compound. The test will detect compounds which inhibit spore germination and/or mycelial growth.

Rhizoctonia and Pythium are tested as a dilute, uniform mycelial suspension. The remaining organisms are tested as a spore suspension in a yeast extract—glucose broth. Compounds are tested at 12 rates in a dilution series. Concentrations are: 50, 25, 12.5, 6, 3, 1.5, 0.75, 0.4, 0.2, 0.1, 0.05, and 0.025 ppm.

This test is designed to measure the MIC's of the compounds for each pathogen. The MIC's are determined from absorbance readings, as described above. An "F" before the MIC value indicates the compound exhibited a fungitoxic effect to that value. An MIC value of 6 ppm or less is considered active. The MIC's for the compounds tested are reported in Table 4.

TABLE 4

| Cmpd # | Fungicidal MIC Results | | | | | | | |
|---|---|---|---|---|---|---|---|---|
| | Organism | | | | | | | |
| | RHI | PYT | COL | HEL | PHY | BOT | PYR | SEP |
| 23 | 0.75 | 0.75 | 0.75 | 1.5 | 3 | F1.5 | 3 | 0.75 |

TABLE 4-continued

| Cmpd # | Fungicidal MIC Results | | | | | | | |
|---|---|---|---|---|---|---|---|---|
| | Organism | | | | | | | |
| | RHI | PYT | COL | HEL | PHY | BOT | PYR | SEP |
| 24 | 0.75 | 0.1 | 0.75 | 1.5 | 1.5 | 1.5 | 3 | 1.5 |

While the invention has been described in detail, various modifications and alterations should become readily apparent to those skilled in the art without departing from the spirit and scope of the invention.

It is claimed:

1. Compounds having the formula:

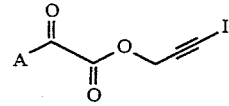

wherein A is selected from the group consisting of substituted or unsubstituted($C_1$–$C_{20}$)alkyl; substituted or unsubstituted phenyl; substituted or unsubstituted ($C_7$–$C_{10}$)aralkyl; substituted or unsubstituted ($C_1$–$C_{20}$) alkoxy; substituted or unsubstituted phenoxy; substituted or unsubstituted benzyloxy; mono($C_1$–$C_{10}$)alkylamino: di($C_1$–$C_{10}$)-alkylamino; ($C_5$–$C_7$)cyclic amino, substituted or unsubstituted anilino; ($C_5$–$C_7$)heterocyclo; and amino substituted with heterocyclic ring.

2. Compounds according to claim 1 wherein A is cyclic amine selected from the group consisting of piperidino, pyrrolidino, and morpholino.

3. Compounds according to claim 1 wherein A is heterocyclic selected from the group consisting of thienyl and furanyl.

4. Compounds according to claim 1 selected from the group consisting of:
   benzoyl formic acid 3-iodo-prop-2-ynyl ester;
   n-octyl oxalamic acid 3-iodo-prop-2-ynyl ester;
   n-propyl oxalamic add 3-iodo-prop-2-ynyl ester;
   thienyl-2-carbonyl formic add 3-iodo-prop-2-ynyl ester;

ethyl 3-iodo-prop-2-ynyl oxalate methyl 3-iodo-prop-2-ynyl oxalate;
phenyl oxalamic add 3-iodo-prop-2-ynyl ester;
pyrrolidine-1-yl-oxo acetic add 3-iodo-prop-2-ynyl ester;
3-methyl-phenyl oxalamic acid 3-iodo-prop-2-ynyl ester;
2-fluoro-4-chloro-5opropargyloxyphenyl oxalamic acid 3-iodo-prop-2-ynyl ester;
4,6-dimethyl-pyrimidin-2-yl oxalamic acid 3-iodo-prop-2-ynyl ester;
piperidine-1-yl-oxo acetic acid 3-iodo-prop-2-ynyl ester;
morpholin-4-yl-oxo-acetic acid 3-iodo-prop-2-ynyl ester;
hexamethylene-imino-1-yl-oxo-acetic acid 3-iodo-prop-2-ynyl ester;
2,6-dimethyl-morpholin-4-yl-oxo-acetic add 3-iodo-prop-2-ynyl ester;
4-methyl-phenyl oxalamic add 3-iodo-prop-2-ynyl ester;
4-chloro-phenyl oxalamic add 3-iodo-prop-2-ynyl ester;
2-chloro-phenyl oxalamic acid 3-iodo-prop-2-ynyl ester;
3-chloro-phenyl oxalamic add 3-iodo-prop-2-ynyl ester;
thiazinan-4-yl-oxo-acetic acid 3-iodo-prop-2-ynyl ester;
thiazolidine-3-yl-oxo-acetic acid 3-iodo-prop-2-ynyl ester;
phenyl 3-iodo-prop-2-ynyl oxalate;
benzyl 3-iodo-prop-2-ynyl oxalate;
and benzyl oxalamic add 3-iodo-prop-2-ynyl ester.

5. Method of controlling the growth of microbes comprising introducing a microbicidally effective amount of one or more compounds according to claim 1 onto, into, or at a locus subject to microbial attack to control microbial growth.

6. Method according to claim 5 wherein said microbe which is being controlled is selected from the group consisting of bacteria, fungi, yeasts, algae, and viruses.

7. Method according to claim 5 wherein said locus is selected from the group consisting of wood, paint, adhesive, glue, paper, pulp/paper slurries, textile, leather, plastics, cardboard, lubricants, cosmetics, food, caulking, feed, and industrial cooling water.

8. Method according to claim 5 wherein the amount of said compound is about 5 to about 300 ppm based on weight of said locus.

9. A composition useful as a microbicide comprising a microbicidally effective amount of a compound according to claim 1 and a carrier.

* * * * *